(12) United States Patent
Weber

(10) Patent No.: US 8,785,210 B2
(45) Date of Patent: Jul. 22, 2014

(54) DETECTION OF AN ANALYTE IN AQUEOUS MEDIA

(75) Inventor: Wolfgang Weber, Berlin (DE)

(73) Assignee: IfP Privates Institut fur Produktqualitat GmbH, Berlin (DE)

( * ) Notice: Subject to any disclaimer, the term of this patent is extended or adjusted under 35 U.S.C. 154(b) by 582 days.

(21) Appl. No.: 12/999,691

(22) PCT Filed: Jun. 17, 2009

(86) PCT No.: PCT/EP2009/057547
§ 371 (c)(1),
(2), (4) Date: Jan. 12, 2011

(87) PCT Pub. No.: WO2009/153293
PCT Pub. Date: Dec. 23, 2009

(65) Prior Publication Data
US 2011/0124126 A1      May 26, 2011

(30) Foreign Application Priority Data
Jun. 18, 2008 (DE) .......................... 10 2008 028 908

(51) Int. Cl.
*G01N 33/543* (2006.01)

(52) U.S. Cl.
USPC ........... 436/518; 436/532; 436/810; 436/501; 436/164; 436/166; 436/536; 436/538; 436/541

(58) Field of Classification Search
USPC ......... 436/518, 532, 810, 501, 164, 166, 536, 436/538, 541
See application file for complete search history.

(56) References Cited

U.S. PATENT DOCUMENTS

| 5,593,824 | A  | * | 1/1997  | Treml et al. ........................ 435/4 |
| 5,958,791 | A  | * | 9/1999  | Roberts et al. ................ 436/514 |
| 6,057,166 | A  | * | 5/2000  | Childs et al. .................. 436/525 |
| 6,207,380 | B1 | * | 3/2001  | Billing-Medel et al. ..... 435/6.14 |
| 6,541,277 | B1 | * | 4/2003  | Kang et al. .................... 436/518 |
| 8,298,834 | B2 | * | 10/2012 | Glezer et al. .................. 436/518 |

(Continued)

FOREIGN PATENT DOCUMENTS

| DE | 10 2006 056 790 | 1/2008 |
| GB | 2457418 | 8/2009 |
| WO | WO 2007/005626 | 1/2007 |

OTHER PUBLICATIONS

Kalogianni et al., "Dry Reagent Dipstick Test Combined With 23S rRNA PCR for Molecular Diagnosis of Bacterial Infection in Arthroplasty," 361 *Anal.Biochem.* 169 (2007).

Glynou et al., "Oligonucleotide-Functionalized Gold Nanoparticles as Probes in a Dry-Reagent Strip Biosensor for DNA Analysis by Hybridization," 75 *Anal.Chem.* 4155 (2003).

(Continued)

*Primary Examiner* — Melanie Y Brown
(74) *Attorney, Agent, or Firm* — James C. Lydon

(57) ABSTRACT

Test kit for the detection of an analyte in an aqueous solution, including chromatographic test strips for a hapten-antihapten complex and first and second standardized vessels for receiving and positioning test strips, which include first and second hapten-coupled receptors against the analyte dried onto the interior wall for the formation of the hapten-antihapten complex, where a portion of the standardized vessels further include a known amount of analyte embedded in a glass-like layer of trehalose, which are dried onto the interior wall of the control vessel so that they dissolve during reaction of the sample with the hapten-coupled receptors. Through this standardization, analytes in unknown samples may be safely detected by immunochromatography within minutes through a hapten-antihapten complex.

13 Claims, 4 Drawing Sheets

(56) References Cited

U.S. PATENT DOCUMENTS

| | | | |
|---|---|---|---|
| 2006/0127907 A1 | 6/2006 | Matsubara et al. | 435/6 |
| 2008/0180259 A1* | 7/2008 | Jung et al. | 340/627 |
| 2009/0269733 A1* | 10/2009 | Khan | 435/5 |
| 2010/0136554 A1* | 6/2010 | Parthasarathy et al. | 435/6 |

OTHER PUBLICATIONS

Soo et al., "Direct and Simultaneous Identification of *Mycobacterium tuberculosis* complex (MTBC) and *Mycobacterium tuberculosis* (MTB) by Rapid Multiplex nested PCR-ICT Assay," 66 *J. Microbiological Methods* 440 (2006).

\* cited by examiner

SEQUENCE LISTING

<160> NUMBER OF SEQ ID NOS: 12

<210> SEQ ID NO 1
<211> LENGTH: 26
<212> TYPE: DNA
<213> ORGANISM: Artificial
<220> FEATURE:
<223> OTHER INFORMATION: DNA-primer

<400> SEQUENCE: 1
gtgaaattat cgccacgttc gggcaa        26

<210> SEQ ID NO 2
<211> LENGTH: 22
<212> TYPE: DNA
<213> ORGANISM: Artificial
<220> FEATURE:
<223> OTHER INFORMATION: 5'-biotin-labelled DNA-primer

<400> SEQUENCE: 2
tcatcgcacc gtcaaaggaa cc        22

<210> SEQ ID NO 3
<211> LENGTH: 21
<212> TYPE: DNA
<213> ORGANISM: Artificial
<220> FEATURE:
<223> OTHER INFORMATION: 5'-digoxigenin-labelled PCR-probe

<400> SEQUENCE: 3
ctctggatgg tatgcccggt a        21

<210> SEQ ID NO 4
<211> LENGTH: 20
<212> TYPE: DNA
<213> ORGANISM: Artificial
<220> FEATURE:
<223> OTHER INFORMATION: DNA-primer

<400> SEQUENCE: 4
ttccttaggt accgtcagaa        20

<210> SEQ ID NO 5
<211> LENGTH: 20
<212> TYPE: DNA
<213> ORGANISM: Artificial
<220> FEATURE:
<223> OTHER INFORMATION: 5'-biotin-labelled DNA-primer

<400> SEQUENCE: 5
ctgcttaaca caagttgagt        20

<210> SEQ ID NO 6
<211> LENGTH: 19
<212> TYPE: DNA
<213> ORGANISM: Artificial
<220> FEATURE:
<223> OTHER INFORMATION: 5'-digoxigenin-labelled PCR-probe

<400> SEQUENCE: 6
tatagtctca tcctacacc        19

<210> SEQ ID NO 7
<211> LENGTH: 22
<212> TYPE: DNA
<213> ORGANISM: Artificial

```
<220> FEATURE:
<223> OTHER INFORMATION: DNA-primer

<400> SEQUENCE: 7
gggatattgt cccctgaaac ag                                              22

<210> SEQ ID NO 8
<211> LENGTH: 19
<212> TYPE: DNA
<213> ORGANISM: Artificial
<220> FEATURE:
<223> OTHER INFORMATION: 5'-biotin-labelled DNA-primer

<400> SEQUENCE: 8
cgagaataag ccgcgcatt                                                  19

<210> SEQ ID NO 9
<211> LENGTH: 18
<212> TYPE: DNA
<213> ORGANISM: Artificial
<220> FEATURE:
<223> OTHER INFORMATION: 5'-digoxigenin-labelled PCR-probe

<400> SEQUENCE: 9
gtagttgtag aggccgtg                                                   18

<210> SEQ ID NO 10
<211> LENGTH: 21
<212> TYPE: DNA
<213> ORGANISM: Artificial
<220> FEATURE:
<223> OTHER INFORMATION: DNA-primer

<400> SEQUENCE: 10
gaaatggaag tgtgagccga t                                               21

<210> SEQ ID NO 11
<211> LENGTH: 22
<212> TYPE: DNA
<213> ORGANISM: Artificial
<220> FEATURE:
<223> OTHER INFORMATION: 5'-biotin-labelled DNA-primer

<400> SEQUENCE: 11
gacatcacta tcaacgaagc aa                                              22

<210> SEQ ID NO 12
<211> LENGTH: 18
<212> TYPE: DNA
<213> ORGANISM: Artificial
<220> FEATURE:
<223> OTHER INFORMATION: 5'-digoxigenin-labelled PCR-probe

<400> SEQUENCE: 12
ggtctgtcgc caacattt                                                   18
```

DETECTION OF AN ANALYTE IN AQUEOUS MEDIA

FIELD OF THE INVENTION

The invention concerns a test kit, based on a test strip for the chromatographic detection of an immune complex with the analyte.

STATE OF THE ART

Lateral-flow immunoassays synergically combine the speed of thin layer chromatography with the selectivity, specificity and sensitivity of immunological detection methods. They are available as test strips for the most wide ranging of applications. They allow a specific detection of antigenic substances and biomolecules. Proteins, peptides, antibodies, antigens, immunogens, autoimmune antigens, carbohydrates, pathogens and germs (bacterial, parasitic, viral, fungal, mycotoxic or toxic), nucleic acids, DNA, RNA, oligo- and polynucleotides, and PCR products may be cited as examples. The test strips are available with different sensitive detection systems, and integrated into systems which facilitate the evaluation of the analysis (see EP 0291194 B2 and references therein). The test strips are also used for the characterisation and identification of foodstuffs, for example in the determination of type and origin of fish (see WO 2002/042416 and references therein).

The test strips for the detection of hapten-antihapten complexes form a particular group, as described for example in US 2002/0119497-A1. In these test strips, a receptor against the first hapten is immobilised on the stationary phase of the thin layer chromatography in the so-called detection zone. Above the stationary separation layer—a thin layer of a very fine grained material, such as silica gel, diatomite, aluminium oxide, cellulose—an adsorption pad is arranged in the chromatographic travelling direction for the adsorption of the mobile phase, and, before that, a control zone with a receptor against the antihapten-antibody. The sample is applied in a region that has been prepared with a dye-labelled antihapten-antibody. The commercially available test packages comprise, apart from the test strip, vessels with antibodies against the analyte, which are conjugated to the corresponding reporter haptens. During the test, the sample is dispersed and taken up into a lysis or elution buffer. If necessary, this is followed by a partial purification of the analyte. Next, two antibodies against the sample analyte, which are coupled to different reporter haptens, are added and a sandwich-immune complex, labelled with two haptens, is formed, but only if there is any analyte present in the sample. The detection complex, doubly labelled with haptens, may then be detected within one minute on the test strip. A particularly common hapten-antihapten system uses biotin and digoxigenin as reporter haptens.

During the chromatographic separation on the test strip, the mobile dye-labelled antihapten antibodies impregnated in the pre-prepared labelling zone (for example monoclonal gold particle-labelled mouse-anti-digoxigenin-IgG) then bind to the detection complex in the detection zone, and then the coloured detection complex is concentrated in a coloured band by an antihapten receptor which is immobilised there, for example avidin or streptavidin, which binds the biotin in the detection complex. A detectable coloured band represents the presence of analyte in the sample. In the given example, polyclonal anti-mouse-Fcg-antibodies (goat-IgG-antibodies against the constant region of the gold-labelled mouse-IgG-antibody) would be immobilised in the control zone and the mobile gold-labelled anti-digoxigenin-antibodies are concentrated therein. The formation of a coloured band in the separation direction above the detection zone represents a successful chromatographic separation. The interpretation of the test strip is then in general carried out according to Table 1.

TABLE 1

| Labelling zone | Detection band | Control band | Result | Comments |
| --- | --- | --- | --- | --- |
| +/− | — | — | No result | Wrong handling of test strip |
| — | X X X | X X X | Positive | High analyte concentration in the sample |
| +/− | XX | X X X | Positive | Sample contains analyte |
| +/− | X | XXX | Weakly positive | Low amount of analyte/unspecific formation of detection complex |
| +/− | — | XXX | Negative | No analyte or no complex formation |
| +/− | — | XX | Negative/unclear | No analyte or no complex formation |
| +/− | — | X | No result | Inhibition of formation of the detection complex and/or inhibition of chromatography (pH, inhibitors or chaotropic substances); sample contains mouse-immunoglobulin |
| +/− | X | — | No result | Chromatography incomplete |

Legend:
XXX intensive colouring;
XX strong colouring;
X weak colouring;
— no colouring;
+/− no or unspecific colouring.

It is not always easy to correctly judge colour and intensity of the bands, in particular, where there is an expectation for a specific result. The elimination of the human factor is extremely important for the practical reliability of a test, because the technically simple test strips shall also be used by untrained or partially trained persons. However, intensive training may not avoid human error, especially in the case of serial testing, high routine, under stress, distraction or sudden disruption. On the other hand, economic factors have to be considered and the cost and time expenditure for the control.

Therefore, a variety of coded frames are suggested in connection with test strips, which are designed to help avoid interpretation errors of the bands. Furthermore, it is suggested to design the colour bands as readable plus and minus-signs (+/−). Still, there remain many possibilities for errors, in particular during sample work-up and the production of the detection complex. The state of the art therefore constitutes a problem.

One object of the invention is to provide a test kit based on the mentioned test strips for a hapten-antihapten detection complex, in which errors in handling and interpretation are ruled out. In particular, one object is to provide a test kit, which uncovers systematic errors in the sample work-up and the formation of the detection complex. Furthermore, it is one aim of the invention to provide a test kit, which allows a follow-up analysis in case of doubt, and which in particular is suited for the quick analysis of foodstuffs for main allergens and germs according to the current EU directives.

BRIEF DESCRIPTION OF THE INVENTION

The problem is solved by a test kit according to claim 1 and the process on which it is based. Preferred embodiments may be derived from the dependent claims.

The test kit comprises a chromatographic test strip with a labelling zone impregnated with mobile labelled antibodies or receptors against a reporter molecule, a detection zone in which a first receptor against a reporter molecule is bound to the stationary phase, and a control zone, which is arranged after the detection zone on the chromatographic line and in which a second receptor against the mobile labelled antibody or receptor is bound to the stationary phase, as well as first and second receptors coupled to reporter molecules for the formation of a detection complex. The test kit is further characterised in that it comprises first labelled vessels for the collection and positioning of chromatographic test strips and second labelled vessels for the collection and positioning of second chromatographic test strips, wherein the first labelled vessels each comprise a known amount of dry analyte, embedded in a water-soluble layer of trehalose, which is dried onto the wall of each first vessel as a thin layer in such a way that, during reaction of the sample with the receptors coupled to the reporter molecule, receptors against the analyte come into contact with the aqueous sample solution, that the water-soluble layer with the known amount of analyte is then immediately dissolved, and that in each first vessel a detection complex with the known amount of analyte is formed, which is detected during chromatographic analysis of the detection complex on the test strip and acts as an internal control for the sample work-up, the complex formation and the chromatographic separation, and wherein the second labelled vessels do not comprise any analyte.

The reporter molecule-coupled receptors against the analyte are preferably antibodies, preferably polyclonal antibodies or different monoclonal antibodies, which are coupled to the corresponding reporter molecules. Lectins may be used as receptors for the detection of glycoconjugates. The reporter molecules are preferably chosen from non-radioactive labels and haptens, such as biotin, digoxigenin, streptavidin, avidin, HRP (horseradish peroxidase), alkaline phosphatase, para-nitrophenol, Texas red, fluorochromes, such as fluorescein, rhodamine, coumarin, and so on.

An unlimited number of hapten-antihapten complexes may be envisaged. Haptens may be visualised with hapten recognising labelling reagents if hapten-coupled primary antibodies are used (or lectins for the detection of glycoconjugates). Exemplary labels are AMCA, TRITC FITC, Cy2, Cy3 and Cy5, and in particular gold particles. Gold-labelled antibodies against the relevant hapten or reporter molecule are particularly preferred. Streptavidin- and anti-biotin-conjugates may also be considered for the detection of biotinylated primary antibodies, while anti-digoxin conjugates easily cross-react with the aglycon digoxigenin and are hence useful for the detection of digoxigenated proteins (Härtig et al., J. Neurosci. Methods 1996, 67, 89-95). Hapten-antihapten processes are advantageous, among others when the use of secondary antibodies against mice would cause the unwanted detection of endogenous immunoglobulins.

In one preferred embodiment, the dye-labelled antibody or receptor in the labelling zone is a gold-labelled monoclonal mouse-antibody against digoxigenin. In the biotin-digoxigenin-system, the first receptor bound in the detection zone of the stationary phase is then streptavidin or avidin. The second receptor, bound on the stationary phase in the control zone, would then for example be a polyclonal goat-antibody against the constant region of mouse-immunoglobulin. The test kit then further comprises, apart from the prepared test strips, further digoxigenated and biotinylated antibodies against the analyte.

In an especially preferred embodiment, the first and second vessels of the test kit further comprise predetermined amounts of reporter molecule-coupled antibodies, embedded in a layer of trehalose on the interior walls of the vessels, which become the reaction vessels. The two hapten-coupled antibodies are preferably separated and also separated from the defined amount of control analyte, and each dried onto the wall of the sample vessel in a separate trehalose solution, under formation of glass-like layers. The respective vessels for the introduction of the aqueous samples with the analyte comprise on the wall defined amounts of hapten-coupled antibodies against the analyte, embedded in a thin glass-like trehalose layer. The hapten-coupled antibodies are preferably present in equimolar amounts, whereby differences in avidity, specificity and sensitivity of the antibodies may be compensated as the case may be, by adapting the amounts or the final concentration in the sample solution. The first vessel, the control vessel, further comprises a defined amount of control analyte, embedded in a layer of trehalose, in addition to the hapten-coupled antibodies.

For carrying out the test, the sample to be analysed is firstly dispersed and taken up into a lysis or elution buffer. If required, a further treatment or work-up of the sample or a partial purification of the analyte follows. Then, equal amounts of a sample solution are introduced into the first and second vessels, the control vessel and the test vessel, the two vessels are briefly shaken, such that the trehalose layers with the antibodies or with the control analyte are dissolved. After the predetermined incubation time with the antibodies, the two test strips are placed in the sample solution and the bands read after termination of the thin layer chromatography.

Alternatively, the hapten-coupled or digoxigenated and biotinylated antibodies against the analyte may be added to both sample solutions. This is less preferred, however, since the addition of two solutions to two reaction vessels is problematic in view of the elimination of the human factor. Serial testing with a high number of samples next to each other then requires extremely high concentration, and it happens all to easily that a reaction vessel is missed out, that a different reaction vessel obtains two additions, that a third vessel gets double amount of one reagent, but not the other one, and so on.

In the inventive test kit with the safety test vessels, such errors are ruled out, because in order to obtain a correct result, it only matters that the vessels receive an aqueous solution with the sample to be analysed. It will be easily seen whether or not a liquid was introduced into a vessel, and a lack of liquid in a sample vessel would be indicated by the chromatography without further work.

Until now, it was unknown to intelligently arrange the positioning and chromatography vessels for a lateral-flow immunoanalysis. So far, the hapten-labelled antibodies for the detection complex were always added to the vessel with the sample in liquid form. The logic of a follow-up analysis using thin layer chromatography is that the detection of the analyte, the detection complex, and the positioning vessel for the thin layer chromatography mentally already form part of the analysis. Furthermore, there was always a danger of solubility and stability problems in the case of dried, hapten-coupled anti-analyte antibodies, and a danger that the detection complex may not be formed. The drying of the hapten-coupled antibodies into the positioning vessel and their combination with a control vessel with a defined amount of control analyte are therefore an elegant solution to the problems.

errors in the sample work-up and the formation of the detection complex. At the same time, errors in the carrying out are ruled out by the test kit, because the test in all its detection steps is designed such that all the steps are carried out in a visibly logical manner. In other words, despite the complexity of the test, all the steps appear logical, even to the untrained user, and they are physically visible, which enhances the trust in the test.

Also, the assessment of the experiment is clearer. The simultaneous assessment of a sample and a control strip does not allow for any gaps in the assessment, as opposed to the single-strip tests of the state of the art. The test kit with the sample vessels and the control vessels and the two test strips reveals every error in the formation of the detection complex and the sample work-up. Table 2 shows the assessment table of the claimed test kit.

TABLE 2

| Test strip | Labelling zone | Detection band | Control band | Assessment/comment |
|---|---|---|---|---|
| Test vessel | +/− | — | — | Wrong handling, no liquid sample, |
| Control vessel | +/− | — | — | negative reaction |
| Test vessel | — | X X X | X X X | Analyte in sample positive |
| Control vessel | — | X X X | X X X | Complexing and detection reactions positive |
| Test vessel | +/− | XX | X X X | Analyte in sample positive |
| Control vessel | +/− | X X X | X X X | Complexing and detection reactions positive |
| Test vessel | +/− | X | X X X | Analyte in sample weakly positive |
| Control vessel | +/− | X X X | X X X | Complexing and detection reactions positive |
| Test vessel | +/− | — | X X X | Analyte in sample negative |
| Control vessel | +/− | X X X | X X X | Complexing and detection reactions positive |
| Test vessel | +/− | — | XX | Error in sample work-up or presence of an |
| Control vessel | +/− | — | X X | inhibitor, since complexing and detection reactions are negative |
| Test vessel | +/− | X | — | Error in sample work-up or detection |
| Control vessel | +/− | X | — | reaction, detection reaction negative |

Legend:
XXX intensive colouring;
XX strong colouring;
X weak colouring;
— no colouring;
+/− no or unspecific colouring.

During the thin layer chromatography, the labelled antibodies against the first hapten (for example, the gold-labelled monoclonal mouse-anti-digoxigenin-antibodies) from the impregnated labelling zone first bind to a detection complex, and then the gold-labelled detection complex is concentrated onto the test strip in the direction of the chromatographic separation in the detection zone by the receptor, which is immobilised there (for example streptavidin, which binds the biotin in the detection complex) in a typically gold-red colour band. The coloured band may then be read. In one band in the control zone, polyclonal anti-mouse-Fcg-antibodies are applied, for example goat-IgG-antibodies against the constant region of the mouse-IgG-antibody, which bind the gold-labelled anti-digoxigenin antibodies of the mobile phase. The formation of a coloured band in the control zone confirms that a separation was achieved on the test strip and that a liquid mobile phase was present in the positioning vessel. However, the band in the control zone only confirms that the chromatographic separation was in principle suitable for detecting a hapten-labelled sandwich complex. Only the control in the control vessel and on the control strip exposes systematic Hence, according to the invention, immunochromatography on the test strips and sample work-up are functionally and visually coupled in a test and a control vessel. While the inclusion of internal controls is known in analytical chemistry, it is new to couple the internal control with a vessel, which according to the user instructions and design is to be used as mechanical positioning device for a chromatographic test strip. Since the sample vessels or positioning devices of the especially preferred embodiments further comprise the essential detection reagents, including the internal control, errors through confusion and missing out of the addition of detection reagents are ruled out. Also, the sample vessels and control vessels may be arranged as vessel pairs, or the standard test strips may include colour codes or mechanical codes, such that they may only be used together with a specific (sample or control) vessel.

The drying of reporter molecule-conjugated antibodies, binding proteins or aptamers in stable form as a vitrified layer onto the wall of sample vessels is known in the art. While there are many possibilities to affix vitrified layers onto the wall of sample vessels (see for example U.S. Pat. No. 5,098,893 by Franks et al., U.S. Pat. No. 6,669,963 by Kampinga et al.) or to render biomolecules more stable in glass-like sugar masses (see for example Rachamachandran et al. in 1$^{st}$ Transdisciplinary Conference on Distributed Diagnosis and Home Healthcare, IEEE Piscataway, N.J., USA, 2006; U.S. Pat. No. 5,593,824 by Treml et al.), such processes in combination with thin layer chromatography of immune complexes are unknown.

The known amount of analyte or the required amounts of reporter molecule-conjugated receptors (antibodies, antibody fragments, binding proteins, RNA, DNA, aptamers) may be dried as a bead in a glass-like layer onto the interior wall of the sample vessel or control vessel from an aqueous solution, to which between 20 and 200 mMol/L trehalose had been added. The drying of the analyte or the receptor amount in a trehalose solution may be carried out at elevated temperature, preferably at a temperature between room temperature and 45° C., and if necessary at slightly reduced pressure, in order to accelerate the drying and vitrification. According to the state of the art, various sugars and macromolecules are also added, in order to suitably adapt the glass transition temperature (see Aksan et al. *Isothermal Desiccation and Vitrification Kinetics of Trehalose-Dextran Solutions* in Langmuir 2004, 5521-5529), or in order to obtain porous, easily soluble, glass-like reagent pearls (see U.S. Pat. No. 5,593,824 by Treml et al.)

The known processes are not suitable for all analytes, in particular not for temperature-sensitive binding molecules and antibodies. Furthermore, they often lead to layers which only dissolve slowly, or in which the desired biomolecules are present in modified form. According to the invention, solutions of the analyte and/or reporter molecule-conjugated receptors, comprising 20 to 600 mM trehalose, preferably 20 to 250 mM trehalose, are separately applied to the interior wall of the sample and the control vessel as droplets, then shock-frozen at −40° C., preferably at −70 to −100° C., such that the trehalose does not crystallise from the solution, and then the droplets are dried by warming to room temperature, wherein the moisture comprised in the droplets is sublimed. Thus, layers or beads of a glass-like, but porous structure are obtained on the interior wall, which firmly adhere to the interior wall of the vessel, and which do not separate or migrate from the wall during transport or shaking of the vessels while transporting and storing them. During the drying process, trehalose displaces the water molecules in the bridging hydrogen bonds with the biomolecules, and renders them stable on the vessel wall for long periods. The shock-freezing of the solution causes the formation of a glass-like trehalose layer, which firmly adheres to the vessel wall, without further procedural steps. The following sublimation of the moisture from the solid, vitrificated layer ensures that it is porous and that, when water or aqueous sample solution is added, it can immediately dissolve.

If the concentration of trehalose in the starting solution is set to a higher value, it may no longer crystallise out and the trehalose-drying also works without the freezing step. A simple drying of the trehalose-containing reagent solution at ambient pressure and 37° C. then gives best results regarding long-time stability and re-solubility of the antibody solutions. The optimum drying time is then about 4 hours. Longer drying times have shown to be detrimental.

Even though not preferred, the antibody solutions may also be dried in multiply concentrated salt and buffer solutions. Normally, antibodies also remain stable and avid after drying from a five-fold PBS-solution, at pH 7.4 (1×PBS=8 g NaCl; 0.2 g KCl; 1.44 g Na$_2$HPO$_4$; 0.24 g KH$_2$PO$_4$ in 1000 mL aqua dest; pH 7.4 with HCl). However, it must be ensured that no migration of the dry substance occurs, and that no insoluble phosphate complexes are formed.

A further variation is to render the reaction of the formation of the detection complex seemingly visible, for example by a parallel, independent colouring reaction of two side components. The two components of the accompanying colouring reaction are preferably dried onto the wall of the reaction and the positioning vessel, separately from the hapten-coupled antibodies. During dissolution of the hapten-coupled antibodies for the detection complex in the sample solution, the components for the accompanying colouring reaction are also dissolved and they may react together. The components of the accompanying colouring reaction are preferably chosen such that the resulting dye is not chromatographically active. If, for example, the chromatographic separation layer contains starch or amylose, the components for the accompanying colouring reaction may be iodine-pyrrolidone complex and amylose, which form a typically deep blue inclusion compound. Two-component dyes or developer dyes may also be used as accompanying components. In many cases, the inclusion of colour-intensive dyes into the trehalose layer will suffice, preferably dyes that have completely different migration behaviour in the chromatographic separation, such as perylene dyes.

By providing ready-to-use test vessels with all reagents and with or without a known amount of control analyte according to the invention, it is further possible to carry out a blind and a positive control, even after carrying out the test and obtaining a first result. This allows the comparing of unclear coloured bands from the experiment with the bands of the blind or the positive control, and allows the safe follow-up interpretation of the first result. Of course, the blind and positive control may be carried out from the start, which considerably facilitates the carrying out of serial tests. The positive and the negative blind tests are also important for the determination of detection limits. These also determine a defined amount of a control analyte on the wall of the control vessel.

Since the significance of consumer protection increases throughout Europe and the world, it is no longer sufficient to test foodstuffs for the presence or absence of one compound, rather the analysis always has to be carried out in a reference system. Also, legal requirements for quality control in the production and use of foodstuffs have consistently risen over the last years, and food producers and traders have to integrate extended quality surveillance procedures into their operational processes. This comprises both analytical testing and the implementation of hygiene and quality management systems.

The inventive test kit offers quick and simple assistance for many problems relevant for analysis and hygiene in the areas of foodstuffs, animal fodders, food additives, and organic products, since analytical limits are assertable for the user through the pre-set internal control and the detection limit, such that an assessment of foodstuffs and their marketability within the legal framework may be carried out with test strip systems. The test kit system according to the invention is therefore adaptable to marketability testing, chemical and microbiological testing, checking of legal declaration duties (whole milk, whole egg, hazelnut, almond, combination of hazelnut and almond, peanut, pistachio, cherry, chickpeas, beans, macadamia, walnut, cashew nut, mustard, celery, soybean, fish in general and specific species, crustaceans and molluscs, grains and cereals), production and routine testing, clearance analytics, microbiological testing for spoilage causing agents, pathogenic or product-specific microorganisms (*salmonella, helicobacter, norovirus, clostridium* and so on), biomolecular testing (allergens, animal species, antibiotics, CNS and BSE through genetic probes and PCR techniques), mycotoxin analytics (detection of aflatoxins, ochratoxin A, DON, patulin, zearalenone).

Further uses are direct stool diagnostics (for example for *salmonella, clostridium difficile* A/B toxins, *norovirus, helicobacter pylori, clostridium*, coeliac disease, and so on) or urine analytics (for example *legionella* sertyp A-soluble protein and others). Apart from the definite determination and the presence of an internal control, one clear advantage of the inventive test kit system is its long shelf life. In particular, there is no danger of the reagents drying out. Furthermore, the test kit system offers the assurance that the reagents are always present in the correct amounts and the correct ratio during sample testing. During drop-wise addition of reagents, there was always the danger of overlooking, mis-counting, swapping or spillage of reagents.

The invention and its embodiments will now be described with the help of examples and with reference to the attached figures.

DETAILED DESCRIPTION OF THE INVENTION

Figure 1:
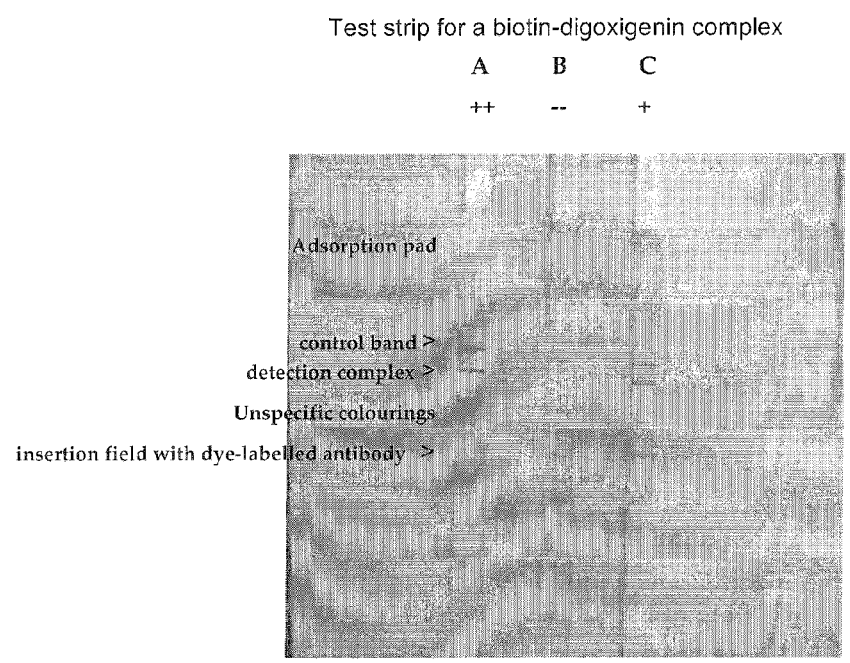
FIG. 1 shows a photograph of three test strips, wherein test strip A tested a sample with an amount of control analyte from the wall of the positioning and sample vessel, test strip B tested the same sample without control analyte and test strip C is a negative sample (without analyte)

The development of the reliable and quick test according to the invention in principally comprises the following steps: (i) immunisation of animals against the analyte and purification of the antibodies; (ii) coupling or conjugating of the purified antibodies with suitable reporter molecules such as biotin and digoxigenin; (iii) testing of the produced antibodies on standard test strips, for example biotin-digoxigenin test strips, and with various samples; and (iv) determination of the detection limit.

In principle, the establishment of a test strip system suffices, since the same reporter molecules (for example biotin and digoxigenin) may be used for the detection of various biomolecules. Therein lies the appeal of the hapten-antihapten system, or of a test strip system based on reporter molecules. Test strips for the detection of sandwich complexes with the haptens biotin and digoxigenin are commercially available. Similarly, packages are available for the biotinylation and digoxigenation of proteins, in particular of antibodies, or also of nucleotides and sugars. Both haptens, biotin and digoxigenin, are also used in the detection of DNA and RNA. In principle, the test according to the present invention may not only be used for the detection of a doubly hapten-labelled sandwich complex, but also for the detection of doubly hapten-labelled PCR products. In this case, the two primers for the PCR-reaction are each labelled with a hapten, for example one with biotin and one with digoxigenin, such that the PCR product carries both haptens. The nucleic acid-complex with the two haptens may then be detected within seconds using thin layer chromatography. In this case, the analyte is DNA or RNA. The reaction with the reporter molecule-coupled receptors corresponds to a DNA-PCR, during which hapten-labelled primers are incorporated into the PCR product.

Commercially available antibodies may of course also be employed against the many different analytes. However, in all cases a definition of the detection limits and the sensitivities, or of the coupling of the antibodies with the reporter molecules remains.

Further advantages and features of the invention may be derived from the following examples.

EXAMPLES

Example 1

Test Kit for the Determination of Whole Egg in Foodstuffs

EU-directives 2003/89/EC and 2005/26/EC require food producers to indicate on their products all ingredients, which may cause food allergies or intolerance, independently of their proportion in the food. So called main allergens are named in particular, including gluten-containing grains (wheat, rye, barley, oat, spelt, kamut and hybrids thereof), crustaceans, eggs and egg products, fish, peanuts, soybean, milk, various types of nuts (almond (*amygdalus communis* I.), common hazelnut (*corylus avellana*), walnut (*juglans regia*), cashew nut (*anacardium occidentale*), pecan nut (*carya illinoiesis* (Wangenh.) K. Koch), Brazil nut (*bertholletia excelsa*), pistachio (*pistacia vera*), macadamia nut and Queensland nut (*macadamia ternifolia*), celery, mustard, sesame seeds and their products, as well as sulphur dioxide. Furthermore, all ingredients have to be disclosed which represent more than 2% of the foodstuff. The choice of the ingredients to be labelled corresponds to the most commonly occurring food allergies and intolerances in Europe. Food allergens generally have to be indicated without any limit in their amount, even if present as traces.

As a representative example, a reliable and quick test for the detection of whole egg (eggs and egg products) in foodstuffs was developed. The development included the steps (i) immunisation of animals, obtaining of a specific antiserum and purification of the IgG fraction of the antiserum using affinity chromatography on a protein-G column; (ii) coupling and labelling of purified antibodies against the analyte with biotin and digoxigenin; (iii) testing of the obtained antibodies on prepared standard biotin-digoxigenin test strip quick tests with different samples; (iv) adaptation and calibration of the internal standard, the amount of analyte on the wall of the sample vessel, to the required detection limit of the test strip.

i) Production of the Antiserum.

Industrial whole egg (100 mg in 1 mL aqua dest) was emulsified with 1 mL Freund's adjuvant, and used to immunise sheep three times in six-week intervals. Six weeks after the last immunisation, raw serum was collected, fatty constituents removed by delipidisation using Aerosil (1.5%), and the immunoglobulins precipitated using ammonium sulphate (2M). The dissolved precipitate was dialysed against 15 mM $KPO_4$, 50 mM NaCl at pH 7.0, and followed by purification of the IgG fraction on a Nab-column (column and method by Pierce, Rockford, Ill. 61105, USA; Kat. Nr. 1940.1, "gravity-flow purification protocol"). The so-called Nab-columns carry immobilised bacterial proteins A, G, A/G and L, which bind mammalian immunoglobulins with high specificity. Finally, empirical testing showed which column was suitable for which type of antibody. In particular, the antibodies were diluted in binding buffer (0.1 M phosphate, 0.15 M NaCl, pH 7.2-protein-G-IgG-binding buffer, Pierce Kat. Nr. 21011), an affinity chromatography column (Nab Protein G Spin Column, Pierce Kat. Nr. 89957) was conditioned with binding buffer, the antiserum was diluted in binding buffer and applied to the column, then the column was washed with binding buffer and neutralised, and the IgG fraction was eluted with elution buffer (0.1 M glycine, pH 2-3: Gentle Ag/Ab elution buffer, Kat. Nr. 21027) and fractionated. The fraction with the highest IgG-content was photometrically determined at 280 nm, the affinity purified antibodies dialysed against PBS and subsequently the solution was set to a protein concentration of 1 mg/mL.

(ii) Coupling of the Purified Antibodies Against Whole Egg with Haptens Digoxigenin and Biotin.

One portion of the purified polyclonal anti-whole egg-antibodies was labelled with digoxigenin and the second portion with biotin. Digoxigenation was carried out using a digoxigenin-labelling kit of Roche Diagnostik GmbH, Mannheim (DIG-Protein Labelling Kit Kat Nr. 11 367 200 001). In particular, digoxigenin-3-0-succinyl-ε-aminocapronic acid N-hydroxysuccinimide ester (DIG-NHS) was dissolved in 50 µL DMSO and added to the antibody solution (1 mL) in a molar ratio of 5:1 (1 antibody molecule per 5 molecules DIG-NHS). The reaction was stopped by addition of L-lysine, and the antibodies were separated by fractionation on a Sephadex-G-25 and dialysis of excess labelling reagent.

Biotinylation was carried out using a biotin labelling kit of Roche Diagnostik GmbH, Mannheim (Biotin Protein Labelling Kit Kat Nr. 11 418 165 001). In particular, D-biotinyl-ε-aminocapronic acid N-hydroxysuccinimide ester (biotin-7-NHS) was dissolved in DMSO and added to the antibody solution (1 mL) in a molar ratio of 5:1 (1 antibody molecule per 5 molecules biotin-7-NHS; 2 hours at room temperature). The reaction was stopped by addition of L-lysine, and the antibodies were separated by fractionation on a Sephadex-G-25, followed by a dialysis of excess labelling reagent. The digoxigenated and biotinylated antibodies were then set to 1 mg/mL PBS, 0.2% sodium azide and frozen.

(iii) Thin-Layer Test Strips for Immune Chromatography.

Figure 2:
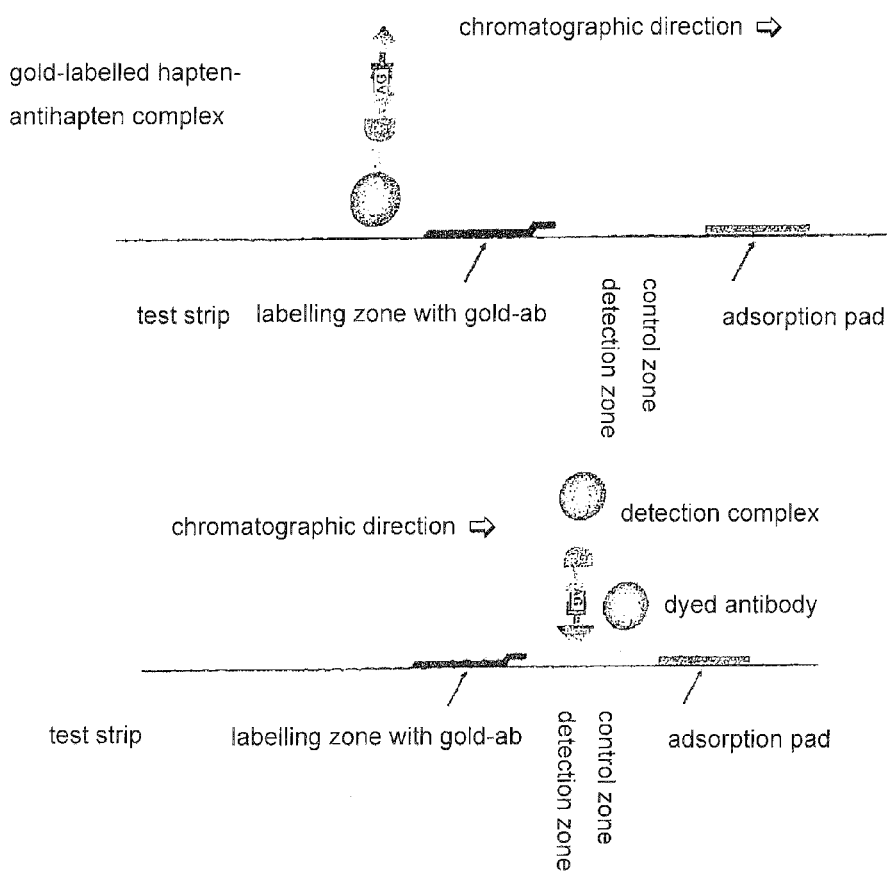
FIG. 2 shows a schematic representation of the detection principle.

Anti-biotin/anti-digoxigenin quick test strips of Roche Diagnostik GmbH, Mannheim were used. On the test strip, the digoxigenin-hapten is dyed with gold-labelled anti-digoxigenin antibodies in the impregnated zone of the quick-test strip. The dyed sandwich complex may then be detected in the immuno-thin layer chromatography through its binding to streptavidin, as described above (see FIG. 2).

(iii) Testing of the Biotinylated and Digoxigenated Anti-Whole Egg-Antibodies on Standard Biotin-Digoxigenin Quick Test Strips.

Different crushed food samples (each 0.5 g), with and without whole egg, were each homogenised in 40 mL PBS for 10 minutes at 60° C., extracted and the solid components removed by centrifugation. For each one, 400 µL supernatant was transferred into a reaction vessel and 2.5 µL each of biotinylated and digoxigenated anti-whole egg-antibody added to each. The sample was mixed and left standing for 10 minutes for the formation of the sandwich complex. Afterwards, quick test strips were positioned into the solution and the result read off after 4 minutes. The sensitivity was below 1 mg whole egg per kg sample (1 ppm) and was therefore clearly more sensitive than conventional ELISA. Main allergens in foodstuffs also have to be declared in the European Union from 1 ppm (see FIG. 1).

(iv) Adaptation and Calibration of the Internal Standards to the Required Detection Limit (1 mg Whole Egg/kg).

Different food compositions from different matrices (nut-nougat cream, dough and baked goods, breadings, flour and potato dumplings, ready sauces, cream foods, vegetable ready-meals, zwieback, pasta dishes, ice cream, ginger bread, chocolate, sweet and sugar wares (candy), ready sauces, deep-freeze meatballs) were tested with regards to the declared and the actually present amount of whole egg. Whole egg standards were produced, corresponding to a content of 1 mg whole egg per kg sample, and adapted to each sample extraction as suggested. In the control vessel, about 10 to 100 ng whole egg (corresponding to 1 to 10 mg per kg foodstuff) was diluted in 5 µL PBS, 45 µL aqueous trehalose 100 mMol/L was added, the solutions mixed and shock-frozen at −60° C., and finally dried onto the base wall of the control vessel as a glass-like layer under warming at 40° C.

Then, in both the sample vessels and the control vessels, 2.5 µL biotinylated or digoxigenated antibodies, mixed with 22.5 µL trehalose 100 mmol/L, were dried upon the walls in a further glass layer through shock freezing at −60° C. and warming to 40° C. Since the differently labelled antibodies may form insoluble complexes together, they were dried separately onto the side wall and the lower surface of the lid of the reaction vessel. In order to render the antibody reaction visible, a trace amount of water-soluble polyvinylpyrrolidone-iodine complex was dried onto the lower surface of the lid next to the antibody solution, and a trehalose/amylose mixture onto the side wall of the vessel.

(v) Immunochromatography.

400 µL whole egg-sample extract was then added into the prepared sample and control vessels, which were closed and inverted several times, in order to dissolve the two antibodies from the walls, including the internal standard. The parallel formation of the characteristic blue colour of the iodine amylose inclusion compound as the vessels were inverted indicated that the reaction vessel with the sample had been inverted, that both antibodies had dissolved and that the sandwich complex for the subsequent detection in the thin layer chromatography was able to form. After a reaction time of 10 minutes, or after full development of the blue colour, the reaction vessels were opened and one test strip was positioned in each of the sample and control vessel in parallel. Since the stationary separation material of the quick test strip comprises starch, as well as diatomite, the blue iodine-amylose inclusion compound did not take part in the thin layer chromatography and could not disrupt the result. The presence of the detection complex could be determined according to Table 2.

Example 2

Test Kit for the Detection of Chickpea

Hazelnut pastes are traded globally on a large scale and are used in a wide variety of foodstuffs. Hazelnut paste and other oil seed products such as almond pulp and pistachio pulp are often blended and adulterated with chickpea pulp, since chickpeas are much cheaper than the oil seeds. A simple quick test would be of great interest to importers and food producers, in order to protect themselves from blending and adulteration. A sensitivity of at least 0.1% (0.1 g chickpea in 100 g oil seed product) was targeted.

i) Production of the Antiserum.

Fine chickpea flour (100 mg in 1 mL aqua dest) was emulsified with 1 mL Freund's adjuvant and used to immunise sheep three times in six-week intervals. Six weeks after the last immunisation, raw serum was collected and the antibodies isolated as in Example 1 and purified by chromatography on a column. The fraction with the highest IgG-content was determined photometrically, the affinity purified antibodies were dialysed against PBS and the solution set to a protein concentration of 1 mg/mL.

(ii) Coupling of the Antibodies Against Chickpea with Digoxigenin and Biotin.

One portion of the purified anti-chickpea antibodies was labelled with digoxigenin and one portion with biotin. Digoxigenation and biotinylation were carried out as shown in Example 1, with the digoxigenin and biotin labelling kits of Roche Diagnostik GmbH, Mannheim (DIG-Protein Labeling Kit Kat Nr. 11 367 200 001; Biotin Protein Labeling Kit Kat Nr. 11 418 165 001). The digoxigenated and biotinylated antibodies were then set to 1 mg/mL PBS, 0.2% sodium azide and frozen.

(iii) Thin Layer-Test Strips for the Immunochromatography.

Anti-biotin/anti-digoxigenin quick test strips of Roche Diagnostik GmbH, Mannheim were used.

(iii) Testing of the Biotinylated and Digoxigenated Anti-Chickpea-Antibodies on Standard Biotin-Digoxigenin Quick Test Strips.

Different hazelnut pastes (each 0.5 g), with and without chickpeas, were each homogenised in 40 mL PBS each for 10 minutes at 60° C., extracted, and the solid components removed by centrifugation. For each, 400 µL supernatant was transferred into a reaction vessel and 5 µL each of biotinylated and digoxigenated anti-chickpea-antibody added. The sample was left for 10 minutes for the formation of the sandwich complex. Afterwards, quick test strips were put into the solution and the result read off after 4 minutes. The sensitivity was below 0.1 g chickpea per 100 g sample (0.1%).

(iv) Calibration of the Internal Standards to the Required Detection Limit (0.1 g Chickpea/100 g).

Different hazelnut pastes were tested and chickpea standards were produced, which corresponded to 0.1 g chickpea per 100 g sample, and adapted to the suggested sample extraction. In the control vessel, about 1 µg chickpea absolute (corresponding to 0.1 g chickpea per 100 g hazelnut paste) was diluted in 5 µL PBS, 45 µL aqueous trehalose 100 mMol/L was added, the solutions mixed and shock-frozen at −60° C., and finally dried onto the base wall of the control vessel as a glass-like layer under warming at 40° C.

Then, in both the sample vessels and the control vessels, 5 µL each of biotinylated or digoxigenated antibodies, mixed with 22.5 µL trehalose 100 mmol/L, were dried onto the side walls and into the lid in a further glass layer through shock freezing at −60° C. and warming to 40° C. In order to also render visible the formation of the detection complex, a trace amount of water soluble polyvinylpyrrolidone-iodine complex was dried onto the lower surface of the lid, and a trehalose/amylose mixture onto the side wall of the vessel.

(v) Immunochromatography.

400 µL hazelnut paste extract was added to both the prepared sample and control vessels, which were closed and inverted several times, in order to dissolve the two antibodies and the standard from the walls. During inversion of the vessels, a blue iodine-amylose inclusion compound was simultaneously formed. After a reaction time of 10 minutes, the reaction vessels were opened and one test strip was positioned in each of the sample and control vessel with the standard, and after 4 minutes, the test strips were read according to Table 2.

Example 3

Determination of *Clostridium difficile* A-Toxin in Stool Samples

*Clostridium* infections are a great danger. Quick diagnosis requires direct detection in stool.

Therefore, a strip test for the detection of *clostridium difficile* A toxin in stool was developed. The development comprised the steps (i) purification of a commercial antiserum (antibody-online, polyclonal goat, 1 mg, ABIN113066) using affinity chromatography on a protein-G column; (ii) coupling of the antibodies with biotin or digoxigenin; (iii) testing of the labelled antibodies using standard biotin-digoxigenin quick test strips with different stool samples; (iv) adapting of the standard on the wall to the required detection sensitivity of the strip tests.

(i) Purification of the Antiserum.

The commercial antiserum was purified on a Nab-column (column and method by Pierce, Rockford, Ill. 61105, USA; Kat. Nr. 1940.1, "gravity-flow purification protocol"), and the IgG-fraction was isolated as in the previous Examples. The affinity-purified antibodies were dialysed against PBS and set to 1 mg/mL.

(ii) Coupling of the *C. Difficile* A Toxin-Antibodies to Digoxigenin and Biotin.

One portion of the purified anti-*C. difficile* A toxin-antibodies was coupled to digoxigenin and one portion to biotin. Digoxigenation and biotinylation were carried out as in Examples 1 and 2.

(iii) Thin Layer-Test Strips for the Immunochromatography.

Anti-biotin/anti-digoxigenin quick test strips of Roche Diagnostik GmbH, Mannheim were used.

(iii) Testing of the Biotinylated and Digoxigenated Anti-*C. Difficile* A Toxin-Antibodies on Standard Biotin-Digoxigenin Quick Test Strips.

Stool samples (each 0.2 g), with and without *C. difficile* A-Toxin, were dispersed in 40 mL PBS each for 10 minutes at 60° C., extracted, and then all solid constituents were removed by centrifugation. For each, 400 µL supernatant was transferred into a reaction vessel and 5 µL each of biotinylated and digoxigenated anti-*C. difficile* A toxin-antibody added to each. The sample was left for 10 minutes for the formation of the detection complex. Afterwards, quick test strips were put into the solution and the result read off after 4 minutes.

(iv) Adaptation and Calibration of the Standard to the Required Detection Limit (1 to 5 µg *C. difficile* A-toxin/g Stool).

Different stool samples were tested and *C. difficile* toxin-A standards were produced. In adaptation to the suggested sample extraction, this required sensitivity corresponded to an amount of 4 to 20 ng *C. difficile* A-toxin absolute in the control vessel. This amount (4 to 20 ng *C. difficile* A-toxin) was diluted in 5 µL PBS, 45 µL aqueous trehalose 100 mMol/L was added, the solutions mixed and shock-frozen at −60° C., and finally dried onto the base wall of the control vessel as a glass-like layer under warming at 40° C.

Then, in both the sample vessels and the control vessels, 5 µL biotinylated or digoxigenated antibodies, mixed with 22.5 µL trehalose 100 mmol/L, were dried upon the walls and the lid in a further glass layer through shock freezing at −60° C. and warming to 40° C. as further glass layers.

(v) Immunochromatography.

400 µL stool extract were added to the prepared sample and control vessels, and the antibodies on the wall and in the lid (with and without standard) were dissolved therein, such that the detection complex for the detection in thin layer chromatography could form. After a reaction time of 10 minutes, test strips were positioned in the sample and the control vessel. The presence of the detection complex was read according to Table 2.

Figure 3A:
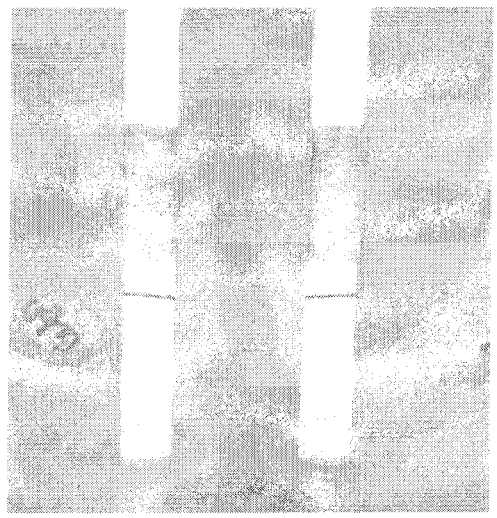
FIG. 3a shows a photograph of two test strips with positive and negative blind samples, wherein the positive blind sample (test strip on the right) represents the lower limit (required-detection limit), and the negative blind sample (test strip on the left) does not contain any analyte.
Figure 3B:
FIG. 3b shows a photograph of four test strips with a comparative pair of negative blind sample and negative sample (pair of test strips on the left) and a comparative pair of positive sample and impregnated positive sample (pair of test strips on the right).

(vi) Follow-Up Determination and Positive and Negative Blind Sample:

Because of the parallel reaction of the sample in the control vessel, a reference band was available, which could be directly compared to the band on the test strip. Therefore an interpretation of the result was always possible. Further, in cases of doubt, a comparison with the bands on a positive and negative blind test could be carried out. The positive and negative blind tests with 1×PBS instead of stool extract may be carried out after a certain time period, as a result of the standardisation of the sample vessels and the chromatographic test strips, which is a considerable advantage (see FIGS. 3a and 3b). FIG. 3a shows the comparison of a positive and a negative blind test, wherein the positive blind test (strip on the right) comprises analyte according to the required detection limit (4 ng C. difficile-toxin). FIG. 3b shows comparisons of a negative stool sample and a negative blind test (comparison pair on the left) and a positive sample with an impregnated positive sample (comparison pair on the right). In the impregnated positive sample, no further band, apart from the control band and the detection band, was displayed, which represents an identification of the detection band. Through those comparisons or follow-up determinations, chromatographic ghost or shadow bands may easily be recognised, and they allow a quantitative assessment of the results.

Hence, there were always comparative bands available, namely (i) from a negative blind test (without analyte in PBS). The negative blind test ensures that the substance is not detected when it is not present. In the negative blind test, only the reagents of the detection process are submitted to the test, without adding them to the substance to be analysed. In this case, the reaction has to be negative. If the reaction happens anyway, the reagents are contaminated and unusable for this determination, or there is a systematic process error. (ii) from a positive blind test (analyte in PBS). The positive blind test ensures that the sought substance is detected if present. The double blind test, i.e. the combination of the positive and the negative blind test, ensures the reliability of the used process. (iii) from a real sample for comparison; and (iv) from a so-called impregnated real-test, in which the detection reaction must occur. If the detection reaction does not occur, the test is unreliable, because either the reagents are aged or because the mixture to be analysed (extract of stool sample) comprises components that inhibit the detection reaction. Since stool samples may be highly different, such a danger must always be considered, in particular for stool samples.

The combination of chromatographic test strips for hapten-antihapten complexes with adapted testing vessels, which comprise reagents as positive and negative blind tests for the formation of the hapten-antihapten complex in an amount determined by the required detection limit allows the provision of a test set, which is directly suitable for the detection of ingredients and germs in foodstuffs and fodders according to the legal requirements. Such a test kit also allows the testing of highly heterogeneous samples of varying consistency, and in particular of stool samples in diagnostics.

Example 4

Test Kit for the Biomolecular Determination of Salmonella in Foodstuffs, Fodders, Veterinary Samples and Other Products Using Probe-Hybridisation and Endpoint Determination on a Quick-Test Strip Salmonella contaminations in foodstuffs occur globally and are the most common cause of diarrhea. Conventionally, determination of the presence or absence of salmonella is carried out by pre-enrichment and selective breeding on specific plates and normally takes 3 to 5 days. There is a high need for faster and more reliable test methods.

A reliable quick-test for the biomolecular determination of salmonella in foodstuffs using probe-hybridisation was developed. The development comprised the steps (i) identification of the primers and the probe; marking of a primer with biotin and of the probe with digoxigenin; (ii) testing of the PCR-product with standard biotin-digoxigenin quick strip tests with DNA standards and various samples; (iii) adaptation and drying of the labelled and unlabelled primer, of the labelled probe and two-fold concentrated amplification buffer (MasterMix); (iv) adaptation and drying of the labelled and unlabelled primer, the labelled probe, of salmonella reference-DNA and two-fold concentrated amplification buffer onto the vessel wall of a 0.2 mL PCR-reaction vessel for the control reaction.

(i) Identification of the Primers and Probe:

The invA gene with the following primers and probe was selected for the determination of salmonella:

```
Sal287 (primer):
5'-gTgAAATTATCgCCACgTTCgggcAA (26-mer),

Sal571_Biotin (primer):
5'-BIO-TCATCgCACCgTCAAAggAACC (22-mer),

Sal invA DIG (probe):
5'-DIG-CTCTggATggTATgCCCggTA (21-mer).
```

(ii) Testing of the PCR-Product with Standard Biotin-Digoxigenin Quick-Test Strips with DNA-Standards and Various Samples, and Adaptation and Drying of the Labelled Oligonucleotides onto the Vessel Wall:

Anti-biotin/anti-digoxigenin quick test strips of Roche Diagnostik GmbH, Mannheim were used. On these quick-test strips, the digoxigenin-PCR-amplificate with gold-labelled anti-digoxigenin-antibodies was applied to the impregnated application zone of the quick strip test. The dyed PCR-product could then be detected in the TLC by its binding to streptavidin. The following method was used:

a) Enrichment of the Food Samples 25 g sample (e.g. chicken or other foodstuffs, fodder, etc.) was pre-enriched in 225 mL buffered peptone water (e.g. Oxoid) and incubated for 18 to 22 h at 37° C. Selective enrichment in Rappaport-Vassiliadis Soya Peptone Broth (RVS; CM0866, Oxoid Limited, Basingstoke, UK) was carried out using 0.1 mL of the pre-enriched sample in 10 mL RVS-solution over 4 to 6 hours at 42° C.

Thermal lysis (release of the salmonella DNA): 1 mL of the enrichment product was transferred into a 2 mL reaction vessel and centrifuged for 5 minutes at 14000 rpm. The supernatant was removed and the pellet that had formed was introduced into 200 µL 0.1×EDTA-buffer, vortexed and lysated for 10 minutes at 95° C. After cooling for 1 to 2 minutes at 4° C., the sample was again centrifuged and the supernatant was again dissolved 1:10 in 0.1×EDTA-buffer solution.

b) PCR and Hybridisation
284 bp

| cycler profile: | 95° C. | 10 min | |
|---|---|---|---|
| | 95° C. | 15 sec | 30 cycles |
| | 67° C. | 60 sec | |
| | 95° C. | 1 min | |
| | 30° C. | 1 min | |

Hybridisation Step

| | | 1× | |
|---|---|---|---|
| amplification buffer 2 × (e.g. Taq) | | 12.5 μL | |
| Sal287 | 10 μM | 0.5 μL | 200 nM |
| Sal571_Biotin | 10 μM | 0.5 μL | 200 nM |
| Sal invA DIG k | 10 μM | 0.5 μL | 200 nM |
| water | | 6 μL | |
| | total | 20 μL | |
| sample/standard DNA | | 5 μL | |
| total in PCR-tube: | | 25 μL | |

After PCR, the PCR-tubes were opened and 150 μL phosphate buffered saline (PBS)-buffer (with 0.1% Tween-20) was directly pipetted in and mixed with the amplificate. A quick-test strip was dipped into the mixture and after 5 seconds, a further 150 μL PBS-buffer (with 0.1% Tween-20) was added. The result could be read after 1 to 2 minutes.

(iii) Adaptation and Drying of the Labelled and Unlabelled Primer, the Labelled Probe and Two-Fold Concentrated Amplification Buffer:

Next, 0.5 μL biotinylated forward primer, 0.5 μL reverse primer and 0.5 μL digoxigenin-labelled probe (each time dissolved in 10 μL trehalose 20 mmol/L) was dried as a glass-layer onto the side wall of a 0.2 mL PCR-reaction vessel at 40° C. over 4 hours. In principle, the two-fold amplification buffer (Taq PCR MasterMix, QIAGEN, Hilden, Del., Cat. Nr. 201443) could also be dried at this stage. This would best be done by freeze-drying, during which the mixture is first frozen to −20° C. and subsequently gently warmed to 10° C. under vacuum.

(iv) Adaptation and Drying of the Labelled and Unlabelled Primer, the Labelled Probe, a *Salmonella* Reference-DNA and Two-Fold Concentrated Amplification Buffer for the Control Reaction:

Next, 0.5 μL biotinylated forward primer, 0.5 μL reverse primer, 0.5 μL digoxigenin-labelled probe and 5 pg *salmonella* reference-DNA (each time dissolved in 10 μL trehalose 20 mmol/L) was dried as a glass-layer onto the side wall of a 0.2 mL PCR-reaction (control) vessel at 40° C. over 4 hours. In principle, the two-fold amplification buffer could also be dried at this stage. This would best be done by freeze-drying, during which the mixture is first frozen to −20° C. and subsequently gently warmed to 10° C. under vacuum.

Figure 4:
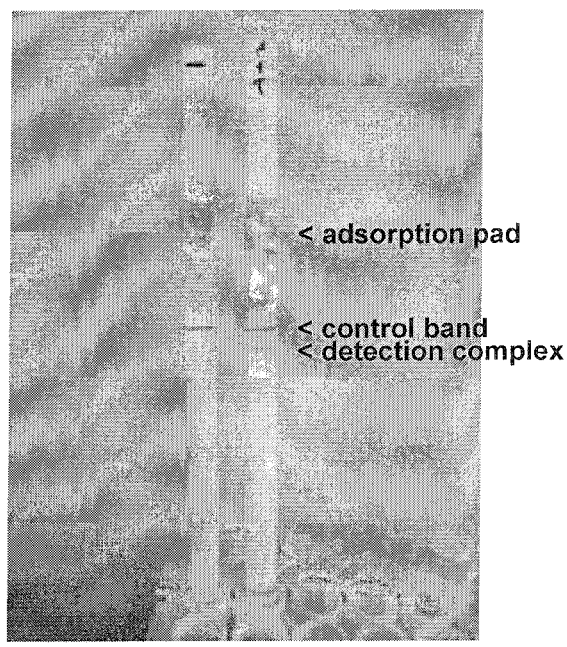
FIG. 4 shows a photograph of two test strips representing the result of determination of the presence of pathogens in analytical samples using PCR, with a negative sample result (strip on the left) and a control strip (strip on the right).

12.5 μL lysated sample or extracted DNA and 12.5 μL two-fold amplification buffer (or, if the amplification buffer has already been dried onto the vessel wall, 25 μL lysated sample) were introduced into the PCR-reaction vessel, and PCR and detection on the quick-test strip were carried out as described above. The detection limit was one salmonellum in 25 g sample. FIG. 4 shows a typical result of the reaction. The strip on the left represents a negative sample after reaction, and the strip on the right represents a positively doped sample (with 1 salmonellum per 25 g sample) after reaction, or a control reaction with *salmonella* reference-DNA pre-dried in the reaction vessel.

Example 5

Test Kit for the Biomolecular Determination of *Campylobacter coli, lari* and *jejuni* (*Campylobacter* from Now Onwards) in Foodstuffs, Fodders, Veterinary Samples and Other Products Using Probe-Hybridisation and Endpoint Determination on a Quick-Test Strip

*Campylobacter* contaminations in foodstuffs occur globally and are one of the most common causes of diarrhea. Conventionally, determination of the presence or absence of *campylobacter* is carried out by pre-enrichment and selective breeding in specific dishes and normally takes 3 to 5 days.

A reliable quick-test for the biomolecular determination of *campylobacter* in foodstuffs using probe-hybridisation was developed. The development comprised the steps of Example 4, with *campylobacter* reference-DNA used in step (iv).

(i) Identification of the Primers and Probe:
A 16S-rRNA gene with the following primers and probe was selected for the determination of *campylobacter*:

```
Cam 18-1 (primer):
5'-TTCCTTAggTACCgTCAgAA (20-mer),

OT 1559-Bio (primer):
5'-BIO-CTgCTTAACACAAgTTgAgT (20-mer),

Cam16S-DIG1 DIG (probe):
5'-DIG-TATAgTCTCATCCTACACC (19-mer).
```

(ii) Testing of the PCR-Product with Standard Biotin-Digoxigenin Quick-Test Strips with DNA-Standards and Various Samples, and Adaptation and Drying of the Labelled Oligonucleotides onto the Vessel Wall:

Anti-biotin/anti-digoxigenin quick test strips of Roche Diagnostik GmbH, Mannheim were used. On these quick-test strips, the digoxigenin-PCR-amplificate with gold-labelled anti-digoxigenin-antibodies was applied to the impregnated application zone of the quick strip test. The dyed PCR-product could then be detected in the TLC by its binding to streptavidin. The following method was used:

a) Enrichment of the Food Samples

A *campylobacter*-selective enrichment solution was produced according to supplier's instructions with Nutrient Broth No. 2 (Catalogue Nr. CM0067), *Campylobacter* Growth Supplement (Liquid; SR0084), PRESTON *Campylobacter* Selective Supplement (SR0117) and Lysed Horse Blood (SR0048; Oxoid Limited, Basingstoke, UK).

25 g (mL) of a food sample was weighed into a sterile Stomacher-bag, diluted 1:10 (w/v) with *Campylobacter* Selective enrichment solution SR0117 "Preston" (Oxoid Limited, Basingstoke, UK) and incubated for 24 h at 42° C. under microaerophilic conditions.

For the DNA-isolation, 1 mL of the incubate was taken and worked-up using a QIAGEN Lambda purification kit (QIAGEN GmbH, Hilden, Del.; Catalogue Nr. 12523).

b) PCR and Hybridisation
287 bp

| cycler profile: | 95° C. | 10 min |
|---|---|---|
| | 95° C. | 15 sec |

Hybridisation Step

|  | | 1× | |
|---|---|---|---|
| amplification buffer 2 × (e.g. Taq) | | 12.5 μL | |
| Cam 18-1 | 10 μM | 0.5 μL | 200 nM |
| OT1559-Bio | 10 μM | 0.5 μL | 200 nM |
| Cam16S-DIG1 | 10 μM | 0.5 μL | 200 nM |
| water | | 6 μL | |
| total | | 20 μL | |
| sample/standard DNA | | 5 μL | |
| total in PCR-tube: | | 25 μL | |

| | | 45 cycles |
|---|---|---|
| 55° C. | 30 sec | |
| 72° C. | 30 sec | |
| 95° C. | 1 min | |
| 30° C. | 1 min | |

After PCR, the PCR-tubes were opened and 150 μL PBS-buffer (with 0.1% Tween-20) was directly pipetted in and mixed with the amplificate. A quick-test strip was dipped into the mixture and after 5 seconds, a further 150 μL PBS-buffer (with 0.1% Tween-20) was added. The result could be read after 1 to 2 minutes.

(iii) Adaptation and Drying of the Labelled and Unlabelled Primer, the Labelled Probe and Two-Fold Concentrated Amplification Buffer:

Next, 0.5 μL biotinylated forward primer, 0.5 μL reverse primer and 0.5 μL digoxigenin-labelled probe (each time dissolved in 10 μL trehalose 20 mmol/L) was dried as a glass-layer onto the side wall of a 0.2 mL PCR-reaction vessel at 40° C. over 4 hours. In principle, the two-fold amplification buffer may also be dried at this stage. This is best done by freeze-drying, in which the mixture is first frozen to −20° C. and subsequently gently warmed to 10° C. under vacuum.

(iv) Adaptation and Drying of the Labelled and Unlabelled Primer, the Labelled Probe, a *Campylobacter* Reference-DNA and Two-Fold Concentrated Amplification Buffer for the Control Reaction:

Next, 0.5 μL biotinylated forward primer, 0.5 μL reverse primer, 0.5 μL digoxigenin-labelled probe and 5 pg *campylobacter* reference-DNA (each time dissolved in 10 μL trehalose 20 mmol/L) was dried as a glass-layer onto the side wall of a 0.2 mL PCR-reaction (control) vessel at 40° C. over 4 hours. In principle, the two-fold amplification buffer could also be dried at this stage. This would best be done by freeze-drying, during which the mixture is first frozen to −20° C. and subsequently gently warmed to 10° C. under vacuum.

Sample analysis was carried out as in Example 4. The detection limit was one *campylobacter* in 25 g sample. FIG. 4 shows a typical result of the reaction.

Example 6

Test Kit for the Biomolecular Determination of *Enterobacter sakazakii* in Milk-Based Baby Food Using Probe-Hybridisation and Endpoint Determination on a Quick-Test Strip

*E. sakazakii* was first described in 1989 as the cause of rare but serious neonatal meningitis, sepsis, or necrotic conditions of the enterocolitis. The highest risk group for *E. sakazakii*-infections are newborn babies and infants, in particular premature infants. Mortality of infants with meningitis is extremely high at 50 to 75%. In many cases, dry-milk baby food was described as the source of the pathogen.

A reliable quick-test for the biomolecular determination of *E. sakazakii* in baby food using probe-hybridisation was developed. The development comprised the steps of Example 4, with *enterobacter* reference-DNA used in step (iv).

(i) Identification of the Primers and Probe:

The transition of the rpsU into the dnaG gene with the following primers and probe was selected for the determination of *enterobacter sakazakii*:

```
Esak-F1 (primer):
5'-gggATATTgTCCCCTgAAACAg (22-mer),

Esak-R1 Bio (primer):
5'-BIO-CgAgAATAAgCCgCgCATT (19-mer),

Esak-S1 DIG (probe):
5'-DIG-gTAgTTgTAgAggCCgTg (18-mer).
```

(ii) Testing of the PCR-Product with Standard Biotin-Digoxigenin Quick-Test Strips with DNA-Standards and Various Samples, and Adaptation and Drying of the Labelled Oligonucleotides onto the Vessel Wall:

Anti-biotin/anti-digoxigenin quick test strips of Roche Diagnostik GmbH, Mannheim were used. On these quick-test strips, the digoxigenin-PCR-amplificate with gold-labelled anti-digoxigenin-antibodies was applied onto the impregnated application zone of the quick strip test. The dyed PCR-product could then be detected in the TLC by its binding onto streptavidin. The following method was used:

a) Enrichment of the Food Samples

A food sample was weighed into a sterile Stomacher-bag, diluted 1:10 (w/v) with sterile deionised water (preheated to 45° C.) and incubated overnight at 37° C. (for example 25 g sample+225 mL water). 10 mL of this pre-incubate were then added to 90 mL enterobacteriaceae incubating solution and incubated for 24 h at 37° C.

For the DNA-isolation, 1 mL of the incubate was taken and worked-up using a QIAGEN Lambda purification kit (QIAGEN GmbH, Hilden, Del.; Catalogue Nr. 12523).

b) PCR and Hybridisation 78 bp

| cycler profile: | 95° C. | 10 min | |
|---|---|---|---|
| | 95° C. | 15 sec | 45 cycles |
| | 67° C. | 60 sec | |
| | 95° C. | 1 min | |
| | 30° C. | 1 min | |

Hybridisation Step

|  | | 1× | |
|---|---|---|---|
| amplification buffer 2 × (e.g. Taq) | | 12.5 μL | |
| Esak-F1 | 10 μM | 0.75 μL | 300 nM |
| Esak-R1 Bio | 10 μM | 0.75 μL | 300 nM |
| Esak-S1 DIG | 10 μM | 0.5 μL | 200 nM |
| water | | 5.5 μL | |
| total | | 20 μL | |
| sample/standard DNA | | 5 μL | |
| total in PCR-tube: | | 25 μL | |

After PCR, the PCR-tubes were opened and 150 μL PBS-buffer (with 0.1% Tween-20) was directly pipetted in and mixed with the amplificate. A quick-test strip was dipped into the mixture and after 5 seconds, a further 150 µL PBS-buffer (with 0.1% Tween-20) was added. The result could be read after 1 to 2 minutes.

(iii) Adaptation and Drying of the Labelled and Unlabelled Primer, the Labelled Probe and Two-Fold Concentrated Amplification Buffer:

Next, 0.5 µL biotinylated forward primer, 0.5 µL reverse primer and 0.5 µL digoxigenin-labelled probe (each time dissolved in 10 µL trehalose 20 mmol/L) was dried as a glass-layer onto the side wall of a 0.2 mL PCR-reaction vessel at 40° C. over 4 hours. In principle, the two-fold amplification buffer could also be dried at this stage. This would best be done by freeze-drying, during which the mixture is first frozen to −20° C. and subsequently gently warmed to 10° C. under vacuum.

(iv) Adaptation and Drying of the Labelled and Unlabelled Primer, the Labelled Probe, an *Enterobacter* Reference-DNA and Two-Fold Concentrate Amplification Buffer for the Control Reaction:

Next, 0.5 µL biotinylated forward primer, 0.5 µL reverse primer, 0.5 µL digoxigenin-labelled probe and 5 pg *enterobacter* reference-DNA (each time dissolved in 10 µL trehalose 20 mmol/L) was dried as a glass-layer onto the side wall of a 0.2 mL PCR-reaction (control) vessel at 40° C. over 4 hours. In principle, the two-fold amplification buffer could also be dried at this stage. This would best be done by freeze-drying, during which the mixture is first frozen to −20° C. and subsequently gently warmed to 10° C. under vacuum.

Sample analysis was carried out as in Example 4. The detection limit was one *enterobacter* in 25 g sample. FIG. 4 shows a typical result of the reaction.

Example 7

Test Kit for the Biomolecular Determination of *Helicobacter pylori* in Stool Samples Using Probe-Hybridisation and Endpoint Determination on a Quick-Test Strip

*Helicobacter pylori*, which lives in the human gastric mucosa, is responsible for a number of gastro-duodenal illnesses, i.e. disorders of the gastro-intestinal tract. Disease patterns comprise chronic-atrophic gastritis and malignant conditions, such as stomach cancer or the MALT lymphoma. Direct determination in stool is often chosen for diagnosis.

A reliable quick-test for the biomolecular determination of *helicobacter pylori* using probe-hybridisation was developed. The development comprised the steps of Example 4, with *helicobacter pylori* reference-DNA used in step (iv).

(i) Identification of the Primers and Probe:

Urease C gene with the following primers and probe was selected for the determination of *helicobacter pylori*:

```
HPure-R (primer):
5'-gAAATggAAgTgTgAgCCgAT (21-mer),

HPureS_Biotin (primer):
5'-BIO-gACATCACTATCAACgAAgCAA (23-mer),

HPure-TM-DIG (probe):
5'-DIG-ggTCTgTCgCCAACATTT (18-mer).
```

(ii) Testing of the PCR-Product with Standard Biotin-Digoxigenin Quick-Test Strips with DNA-Standards and Various Samples, and Adaptation and Drying of the Labelled Oligonucleotides onto the Vessel Wall:

Anti-biotin/anti-digoxigenin quick test strips of Roche Diagnostik GmbH, Mannheim were used. On these quick-test strips, the digoxigenin-PCR-amplificate with gold-labelled anti-digoxigenin-antibodies was applied to the impregnated application zone of the quick strip test. The dyed PCR-product could then be detected in the TLC by its binding onto streptavidin. The following method was used:

a) Extraction from Stool Samples

For DNA-extraction from a stool sample, the supplier instructions of a QIAGEN QIAamp DNA Stool Kit were followed (QIAGEN GmbH, Hilden, Del.; Catalogue Nr. 51504).

b) PCR and Hybridisation 92 bp

| cycler profile: | 95° C. | 10 min | |
|---|---|---|---|
| | 95° C. | 15 sec | 45 cycles |
| | 62° C. | 60 sec | |
| | 95° C. | 1 min | |
| | 30° C. | 1 min | |

Hybridisation Step

| | | 1× | |
|---|---|---|---|
| amplification buffer 2 × (e.g. Taq) | | 12.5 µL | |
| HPure-R | 10 µM | 0.25 µL | 100 nM |
| HPure-S-Biotin | 10 µM | 0.25 µL | 100 nM |
| HPure-TM-DIG | 10 µM | 0.25 µL | 100 nM |
| water | | 6.75 µL | |
| total | | 20 µL | |
| sample/standard DNA | | 5 µL | |
| total in PCR-tube: | | 25 µL | |

After PCR, the PCR-tubes were opened and 150 µL PBS-buffer (with 0.1% Tween-20) was directly pipetted in and mixed with the amplificate. The quick-test strip was dipped into the mixture and after 5 seconds, a further 150 µL PBS-buffer (with 0.1% Tween-20) was added. The result could be read after 1 to 2 minutes.

(iii) Adaptation and Drying of the Labelled and Unlabelled Primer, the Labelled Probe and Two-Fold Concentrated Amplification Buffer:

Next, 0.5 µL biotinylated forward primer, 0.5 µL reverse primer and 0.5 µL digoxigenin-labelled probe (each time dissolved in 10 µL trehalose 20 mmol/L) was dried as a glass-layer onto the side wall of a 0.2 mL PCR-reaction vessel at 40° C. over 4 hours. In principle, the two-fold amplification buffer could also be dried at this stage. This would best be done by freeze-drying, during which the mixture is first frozen to −20° C. and subsequently gently warmed to 10° C. under vacuum.

(iv) Adaptation and Drying of the Labelled and Unlabelled Primer, the Labelled Probe, a *Helicobacter* Reference-DNA and Two-Fold Concentrated Amplification Buffer for the Control Reaction:

Next, 0.5 µL biotinylated forward primer, 0.5 µL reverse primer, 0.5 µL digoxigenin-labelled probe and 5 pg *helicobacter* reference-DNA (each time dissolved in 10 µL trehalose 20 mmol/L) was dried as a glass-layer onto the side wall of a 0.2 mL PCR-reaction vessel at 40° C. over 4 hours. In principle, the two-fold amplification buffer could also be dried at this stage. This would best be done by freeze-drying, during which the mixture is first frozen to −20° C. and subsequently gently warmed to 10° C. under vacuum.

Sample analysis was carried out as in Example 4. The detection limit was one *helicobacter* in 25 g sample. FIG. 4 shows a typical result of the reaction.

The invention claimed is:

1. Test kit based on chromatographic test strips for the detection of a known hapten-antihapten complex, comprising
- a plurality of test strips each comprising a strip-shaped carrier coated with a thin layer of a chromatographic separation material comprising
- a labelling zone impregnated with mobile reporter molecule-labelled antibodies or receptors against a first hapten;
- a detection zone, in which a receptor against a hapten has been immobilised; and
- a control zone, in which a second receptor against the mobile reporter molecule-labelled antibody or receptor has been immobilised;
- in combination with one or more first and second vessels for receiving and positioning said test strips, said first and second vessels each containing first and second hapten-coupled receptors against the analyte for the formation of a hapten-antihapten complex, wherein each first vessel further comprises a known amount of analyte, embedded in a glass-like trehalose layer which is dried onto an interior wall of the first vessel as a layer in such a way that the layer dissolves in an aqueous sample solution during reaction of the sample with the hapten-coupled receptors, such that in the first vessel there is always a pre-determined amount of detection complex, which becomes visible during chromatographic analysis of the test strip and provides a control for the sample work-up, the complex formation and the chromatographic analysis, and wherein the second vessels do not comprise a known amount of analyte, wherein the known amount of analyte in the first vessel corresponds to a required detection limit, which is visible as a hapten-antihapten complex on the test strip, and wherein the first and second vessels comprise pre-determined amounts of hapten-coupled receptors against the analyte, which are dried in such a way that they dissolve upon addition of the aqueous sample.

2. Test kit according to claim 1, wherein predetermined amounts of at least two hapten-coupled receptors and optionally of the analyte have each been embedded in a glass-like trehalose layer and dried at different places onto the interior wall of the vessels.

3. Test kit according to claim 1, wherein predetermined amounts of at least two hapten-coupled receptors and optionally of the analyte have each been embedded in a glass-like trehalose layer and dried in separate layers onto the interior wall of the vessels.

4. Test kit according to claim 1, wherein a known amount of analyte or receptor has been applied to the vessel wall by drying onto the vessel wall a defined amount of an aqueous solution comprising the receptor or the analyte, which solution comprises 20 to 600 mMol/L trehalose, through shock-freezing and subsequent water-sublimation.

5. Test kit according to claim 1, wherein the addition of hapten-coupled receptors against the analyte in the sample and/or control vessel is carried out by drying their aqueous solutions comprising between 20 and 600 mMol/L trehalose, onto the interior wall of the sample and control vessels at a temperature between room temperature and 45° C.

6. Test kit according to claim 1, wherein the receptors are chosen from antibodies, antibody fragments, lectins, binding proteins, DNA, RNA, or aptamers coupled to reporter molecules.

7. Test kit according to claim 1, wherein the reporter molecules are chosen from biotin, digoxigenin, digoxin, streptavidin, avidin, HRP (horseradish peroxidase), alkaline phosphatase, para-nitrophenol, Texas red, fluorochromes, fluorescein, rhodamine, coumarin, AMCA, TRITC FITC, Cy2, Cy3 and Cy5.

8. Test kit according to claim 1, based on a hapten-antihapten system, comprising biotin or digoxigenin-coupled primary antibodies.

9. Test kit according to claim 1, further comprising components for an independent coloring reaction, wherein said components are dried on an interior wall of said first and second vessels.

10. Test kit according to claim 1, comprising extraction reagents for the detection of main allergens in foodstuffs and fodders.

11. Test kit according to claim 1, comprising extraction means for the extraction of an analyte from stool or smears.

12. Process for the detection of an analyte in an aqueous solution in which a dye-labelled hapten-antihapten complex with the analyte is detected in a thin layer chromatography on a test strip, comprising aliquoting an aqueous solution comprising the sample into at least a first and a second vessel, wherein the first and the second vessel are adapted to receive test strips, the first vessel comprising a predetermined amount of analyte and predetermined amounts of at least two hapten-coupled receptors against the analyte, each embedded in glass-like trehalose layers, which have been dried onto the interior wall of the vessel, wherein the predetermined amount of analyte in said first vessel corresponds to a required detection limit, which is visible as a hapten-antihapten complex on the test strip;

the second vessel also comprises equal predetermined amounts of at least two hapten-coupled receptors against the analyte, each embedded in glass-like trehalose layers which have been dried onto the interior wall of the vessel, and the test strips each comprise a strip-shaped carrier coated with a thin layer of a chromatographic separation material comprising a labelling zone impregnated with mobile reporter molecule-labelled antibodies or receptors against a first hapten;

a detection zone, in which a receptor against a hapten has been immobilised; and a control zone, in which a second receptor against the mobile reporter molecule-labelled antibody or receptor has been immobilised, dissolving in the first and second vessel the trehalose layers with the predetermined amounts of at least two hapten-coupled receptors in the corresponding aliquot of the sample solution and producing conditions for the formation of a hapten-antihapten complex with the analyte, and detecting the hapten-antihapten complex in the sample solution through its dye-labelling and a thin layer chromatography using test strips, which are placed or dipped into the first and second vessels with the sample solution, by comparison of the coloured bands in the detection zones of the test strips from the first and second vessels.

13. Process according to claim 12, wherein the aqueous solution does not contain a sample and coloured bands for a positive and a negative blind test are provided.

* * * * *